United States Patent
Yonak et al.

(10) Patent No.: US 6,227,036 B1
(45) Date of Patent: May 8, 2001

(54) MULTIPLE MICROPHONE PHOTOACOUSTIC LEAK DETECTION AND LOCALIZATION SYSTEM AND METHOD

(75) Inventors: Serdar H. Yonak, Jackson; David R. Dowling, Ann Arbor, both of MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/181,283

(22) Filed: Oct. 28, 1998

(51) Int. Cl.[7] .......................... G01M 3/08; G01N 29/00; G01N 15/06
(52) U.S. Cl. .................... 73/40.5 A; 73/601; 250/573
(58) Field of Search ............... 73/40.5 A, 40.7, 73/601; 250/573

(56) References Cited

U.S. PATENT DOCUMENTS

| 4,457,162 | 7/1984 | Huebler et al. . |
| 4,512,371 | 4/1985 | Drzewiecki et al. . |
| 4,516,858 | 5/1985 | Gelbwachs ........................... 356/437 |

FOREIGN PATENT DOCUMENTS

| 8815653 | 11/1988 | (AU) . |
| 4446723 | 1/1996 | (DE) . |
| 19516974 | 10/1996 | (DE) . |
| 151474 | 8/1985 | (EP) . |
| 55-010533 | 1/1980 | (JP) . |
| 55-010534 | 1/1980 | (JP) . |
| 55-010535 | 1/1980 | (JP) . |
| 55-010536 | 1/1980 | (JP) . |
| 55-010576 | 1/1980 | (JP) . |
| 55-015022 | 2/1980 | (JP) . |
| 55-050142 | 4/1980 | (JP) . |
| 59-184539 | 10/1984 | (JP) . |
| 61-254834 | 11/1986 | (JP) . |
| 5-312716 | 11/1993 | (JP) . |
| 8-271336 | 10/1996 | (JP) . |
| 86/04746 | 8/1986 | (WO) . |
| 90/02935 | 3/1990 | (WO) . |
| 96/21850 | 7/1996 | (WO) . |
| 96/24831 | 8/1996 | (WO) . |

OTHER PUBLICATIONS

Kreuzer and Patel, 1971, "Nitric Oxide Air Pollution: Detection by Optoacoustic Spectroscopy", Sciece, vol. 173, 45–47.

Claspy, 1977, "Infrared Optoacoustic Spectroscopy and Detection", Optoacoustic Spectroscopy and Detection, pp. 133–166.

Lord Rayleigh, 1881 "The Photophone". Nature, vol. 23, 274–275.

Bell, 1880, "On the Production and Reproduction of Sound by Light", American Journal of Science, vol. 20, 305–324.

(List continued on next page.)

Primary Examiner—Hezron Williams
Assistant Examiner—Jay L. Politzer
(74) Attorney, Agent, or Firm—Barbara M. Burns

(57) ABSTRACT

A method and system for multiple microphone photoacoustic leak detection and localization. The leak detection technique uses photoacoustic sounds produced by the interaction of a carbon dioxide (CO2) laser turned to 10.6 microns and a photoactive tracer gas, sulfur hexafluoride ($SF_6$), emitted by calibrated leak sources. As the leaked gas is heated by the laser, it expands and launches a photoacoustic sound pulse. The sound pulses generated by the scanning process are recorded across a broad bandwidth by multiple ultra-sensitive microphones. After the photoacoustic pulses arc recorded, the magnitude is compared with background noise measurement at several frequencies for a determination if a leak is present. If the presence of a leak is found, then the location of the leak is determined. The recorded sound is processed by using Matched Field Processing (MFP) as the signal processing technique. The photoacoustic sounds recorded at the microphones are reversed in time through computer simulation that causes the sounds to converge to the apparent point of origin. No synchronization between the acoustic signal processor and the laser scanner is required.

20 Claims, 12 Drawing Sheets

U.S. PATENT DOCUMENTS

| | | |
|---|---|---|
| 4,557,603 | 12/1985 | Oehler et al. .......................... 356/418 |
| 4,622,845 | 11/1986 | Ryan et al. ............................... 73/24 |
| 4,806,760 | 2/1989 | McGlade . |
| 4,866,681 | 9/1989 | Fertig . |
| 4,903,248 | 2/1990 | Fertig . |
| 4,921,346 | 5/1990 | Hirishi et al. . |
| 4,995,011 * | 2/1991 | Spiesberger .......................... 367/127 |
| 5,161,408 | 11/1992 | McRae et al. ......................... 73/40.7 |
| 5,355,312 * | 10/1994 | Tolstoy et al. .......................... 702/18 |
| 5,417,113 | 5/1995 | Hartley ................................... 73/587 |
| 5,544,074 | 8/1996 | Taniguchi et al. .................... 364/508 |
| 5,576,480 | 11/1996 | Hopkins et al. .......................... 73/38 |
| 5,581,017 | 12/1996 | Bejtlich, III .............................. 73/38 |
| 5,780,724 * | 7/1998 | Olender et al. .................... 73/40.5 A |
| 5,834,632 * | 11/1998 | Olender et al. ........................ 73/40.7 |
| 5,917,193 * | 6/1999 | Schroff et al. ......................... 250/573 |

OTHER PUBLICATIONS

Jackson and Dowling, 1991, "Phase conjugation in underwater acoustics," J. Acoust. Soc. Am., vol. 89, 171–181.

Laser–generated acoustic emission detects gas leaks, Laser World Focus, February 1998.

Tyndall, 1881 "Action of an Intermittent Beam of Radiant Heat upon Gaseous MAtter", Proceedings of the Royal Society of London, vol. 31, 307–317.

Bell, 1881, "Upon the Production of Sound by Radiant Energy", Philosophical Magazine, vol. 11, 510–528.

Mercadier, 1881, "On Radiophony", Philosophical Magazine, vol. 11 78–80.

Preece, 1881, "On the Conversion of Radiant Energy into Sonorous Vibrations"., Proceedings of the Royal Society of London, vol. 31, 506–520.

Fialkowski et al., 1997, "Source localization in noisy and uncertain ocean environments," J. Acoust. Soc. Am., vol. 101, 3539–3545.

Perkins et al., 1990, "Environmental signal processing: Three dimensional matched field processing with a vertical array," J. Acoust. Soc. Am., vol. 87, 1553–1556.

Jensen et al. 1994, "Computational Ocean Acoustics," (American Institute of Physics, New York), Ch. 10.

Lyman et al., 1986, "Single–infrared–frequency studies of multiple photon excitation and dissociation of polyatomic molecules," in Multiple–Photon Excitation and Dissociation of Polyatomic Molecules, edited by C.D. Cantrell (Springer Verlag, Berlin), pp. 9–94.

Dewey, 1974, "Opto–Acoustic Spectroscopy," Optical Engineering, vol. 13, 183–488.

Dewey, et al., 1973, "Acoustic Amplifier for Detection Atmospheric Pollutants", Applied Physics Letters, vol. 23, 633–635.

Goldan and Goto, 1974, "An Acoustically Resonant System for Detection of Low–Level Infrared Absorption in Atmospheric Pollutants," Journal of Applied Physics, vol. 45, 4350–4355.

McRae, 1994, "Photo Acoustic Leak Location and Alarm on the Assembly Line," Materials Evaluation, vol. 52, 1186–1190.

Baggeroer, et al., 1993, An Overview of MAtched Field MEthods in Ocean Acoustics, IEEE Journal of Oceanic Engineering, vol. 18, 401–424.

Bucker, 1976, "Use of Calculated Sound Fields and Matched–Field Detection to Locate Sound Sources in Shallow Water," J. Acoust. Soc. Am., vol. 59, 368–373.

Collins et al., 1991, "Foalization: Environmental focusing and source localization," J. Acoust. Soc. Am., vol. 90, 1410–1422.

Collins, 1994, "Noise cancellation and source localization," J. Acoustic. Soc. Am., vol. 96, 1773–1776.

Brassington, 1982, "Photo–acoustic Detection and Ranging–A New Technique for the Remote Detection of Gases," Journal of Physics D: Applied Physics, vol. 15, 219–228.

Kreuzer, 1977, The Physics of Signal Generation and Detection, Optoacoustic Spectroscopy and Detection, Academic Press, New York, pp. 1–25.

Baggeroer et al., 1988, "Matched Field Processing: Source Localization in Correlated Noise as an Optimum Parameter Estimation Problem," J. Acoust. Soc. Am., vol. 83, 571–587.

* cited by examiner-

MULTIPLE MICROPHONE PHOTOACOUSTIC LEAK DETECTION AND LOCALIZATION SYSTEM AND METHOD

BACKGROUND OF THE INVENTION

The field of the invention relates to the problem of gas leaks. In particular, the invention pertains to a method and system for detection and location of leaks from various pressurized components.

Many industrial and domestic machines use or convey pressurized gases or liquids. Leaks from these machines may be costly to consumers as well as manufacturers, and moreover, depending on the composition of the gas or liquid, the leaks could be harmful to the environment.

Heretofore, several methods of leak testing have been employed. Methods such as bubble visualization, sniffing, pressure decay, evacuating the part to create a vacuum and surrounding the part with a gas and checking for any intrusion of the gas into the part, pressurization/immersion, pressurization/soaping, and pressurization/ammonia sensitive painting are some of the various techniques that have been used with varying degrees of success. Most of these techniques and their drawbacks are described in U.S. Pat. No. 5,161,408 to McRae, et al. The McRae et al. patent discusses a photo-acoustic leak detection system and method that employs a single microphone and narrowband signal processing. Photo-acoustics is the excitation of acoustic waves by unsteady heat addition from a light source. This phenomena was discovered more than a century ago. Photo-acoustics has been used primarily for spectroscopy and most measurements have been made in closed acoustically resonant cells.

Despite the need for a method and system for photoacoustic detection and localization of leaks, especially small leaks, without the necessity of synchronization and with the use of broadband matched-field signal processing, none was known. Thus, there existed the need for a method and system for photoacoustic detection and localization of leaks without synchronization and with the use of broadband matched-field signal processing.

The disclosed method and system of this invention is applicable to a wide range of leak problems, including but not limited to consumer or industrial products such as automobile components, refrigerators, air conditioners and electrical equipment that includes parts that contain liquids or pressurized gases.

The present method and system does not require synchronization, and uses broadband matched-field signal processing across all signal frequencies. The method and system are described below.

SUMMARY OF THE INVENTION

It is an object of the invention to provide a method and system for photoacoustic leak detection and localization.

It is an object of the invention to use Matched Field Processing (MFP) for signal processing which technique was originally developed for use in underwater acoustics.

The present system and method for photoacoustic leak detection and localization has several innovative features. The first innovation is the use of multiple ultra-sensitive microphones for detecting the photoacoustic sound emitted by the tracer gas when excited by the collimated light. While a single microphone has been employed in the past, the present system uses multiple ultra-sensitive microphones for sound detection. The second innovation is the detection of the sound and combination of signals from the sound across a broad bandwidth, the broadband allowing for multiple frequencies across all signal frequencies. The third innovation is non-synchronous processing of the signal wherein the signal processing is not connected to the beam scanning means. Matched Field Processing is employed to determine the actual leak location. In the prior art, particularly, the McRae et al. Patent, synchronous processing with regard to the scan positioning signal output was required.

Leaks from pressurized containers cause problems with the environment, consumers and manufacturers. The invention is a leak detection technique employing photoacoustic sounds produced by the interaction of a carbon dioxide (CO2) laser turned to 10.6 microns with a photoactive tracer gas, sulfur hexafluoride ($SF_6$), emitted by calibrated leak sources. Sulfur hexafluoride ($SF_6$) gas is inert, non-toxic and safe for use in occupied human environments.

The part being tested is filled with the gas and if a leak exists, a cloud of the gas will form near the leak. Each time the laser scans the part and encounters a cloud of tracer gas, the gas is heated and expands and launches a photoacoustic sound pulse. The sound pulses generated by the scanning process are recorded by multiple ultra-sensitive microphones. The human ear can hear the photoacoustic sound from large leaks, even though the a majority of the sound produced occurs at frequencies beyond the audible range. However, photoacoustic sound from small leaks is not detectable by the human ear, requiring the ultra-sensitive microphones.

After the photoacoustic pulses are recorded, the magnitude is compared with background noise measurement at several frequencies for a determination if a leak is present. If the presence of a leak is found, then the location of the leak is determined. The recorded sound is processed by using Matched Field Processing (MFP) as the signal processing technique. Knowledge of the acoustic characteristics of the surroundings is necessary for use of the MFP technique. The MFP technique is capable of handling the output of any number of microphones across many signal frequencies.

The location of the microphones with respect to the test part, the speed of sound, and the location and approximate shape of objects that can cause echoes must be known. The photoacoustic sounds recorded at the microphones are reversed in time through computer simulation and cause the sounds to converge to the apparent point of origin.

Measured acoustic signals are compared to predicted acoustic signals to produce an ambiguity surface based on a computational model of the acoustic environment with a variable test source location. When there is a good match between the predicted and measured acoustic signals, the ambiguity surface achieves a maximum and the test source is presumed to be at or near the location of the actual acoustic source. In this sense, the MFP ambiguity surface can be thought of as a spatial correlation, which when normalized properly gives a probability map for the source location. The accuracy of the MFP-determined sound-source location is strongly dependent on the accuracy of the acoustic model of the environment and the signal-to-noise ratio of the measurements. Hence, source localization to better than a wavelength may be possible with a good environmental model at high signal-to-noise ratios. Generally MFP has been developed as a narrowband technique, but broadband source localization by incoherently combining MFP results from several frequencies is a straight forward extension (Baggeroer et al., 1988).

Two particular implementations of MFP do not require a priori information about background noise: the Bartlett processor (Bucker, 1976) which is technically equivalent to back-propagation or time-inversion of the received signals (Jackson and Dowling 1991), and the minimum variance (MV) distortionless processor (described in Jensen et al. 1994) which typically provides better side lobe control than the Bartlett processor when the signal-to-noise ratio comfortably exceeds 0 dB. Although more sophisticated MFP schemes exist (Collins and Kuperman 1991, Collins et al. 1994, Fialkowski et al. 1997). The two implementations herein described are relatively easy to implement and provide important baseline results for photoacoustic leak localization. But other MFP techniques can be used.

A carbon dioxide laser tuned to 10.6 microns and the tracer gas sulfur hexafluoride ($SF_6$) are used to produce photoacoustic sounds. The laser beam is rapidly scanned across a flat plate (or parallel to the part) with a leak of known-rate present or absent along the scan. Acoustic measurements are made with two or four microphones and the recorded signal is Fourier analyzed and compared to a previously measured background sound level at the harmonics of the scan rate (the signal frequencies). If the recorded signal exceeds the background level by more than a factor of three, a positive detection is made and a leak is presumed to be present. Since the source has broadband characteristics, MFP is performed at the main signal frequencies and the ambiguity surfaces from the various frequencies are incoherently averaged. The peak of the resultant multiple-frequency ambiguity surface is used to determine the location of the leak. Reflecting boundaries and frequency-dependent microphone directionality are accounted for in the processing. It is to be noted that the laser can be non-contacting with the part.

For a more complete understanding of the present invention, reference is made to the following detailed description when read with in conjunction with the accompanying drawings wherein like reference characters refer to like elements throughout the several views, in which:

DESCRIPTION OF THE PREFERRED EMBODIMENT

Multiple ultra-sensitive microphones are used for detecting the photo acoustic noise emitted by the tracer gas when excited by the collimated light. Photo acoustic noise is detected across a broad bandwidth. Non-synchronous processing of the signal using Matched Field Processing to determine the actual leak location does not require connection to the beam scanning means. The prior art required synchronous processing with regard to the scan positioning signal output.

Figure 1:
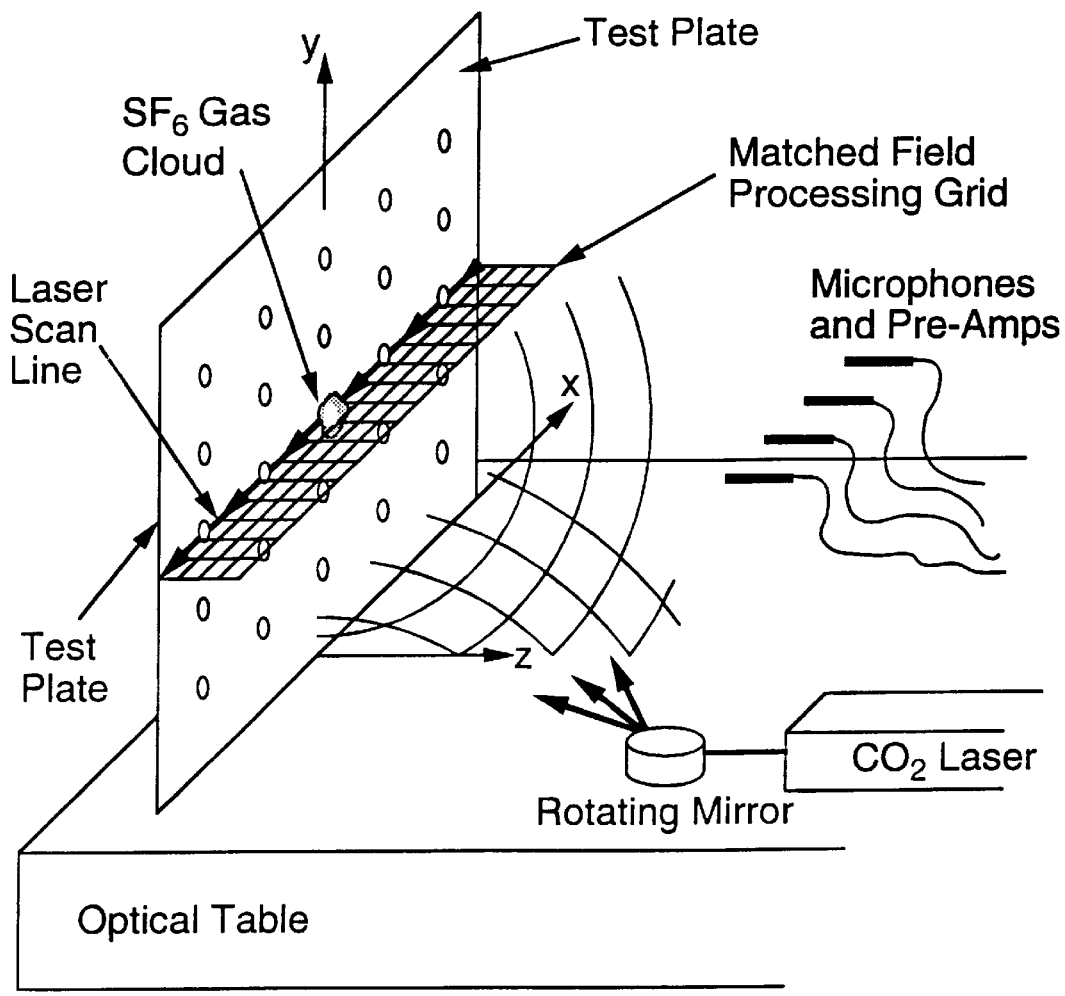
FIG. 1 illustrates a representation of the system according to the invention.

Now turning to FIG. 1, thereshown is a representation of the system for a one-dimensional detection and localization of leaks along a line parallel to the x-axis on a flat a luminum plate mounted on top of and perpendicular to an optical table. The environment, consisting primarily of painted cinder block walls with a concrete ceiling and a tile floor, was not acoustically treated. The temperature was monitored to ±1° C. using a T-type thermocouple and an electronic signal conditioner. The plate measures 0.61 m by 0.61 m and has holes which a re spaced evenly on 7.62 cm centers. Leak detection and localization was investigated on the bottom row of holes, located 10.5 cm above the table surface. For detection and localization in a factory on a two dimensional surface, the second in-plane dimension (corresponding to the y-coordinate) would be interrogated by assembly-line motion. A known-rate leak of the tracer gas, $SF_6$, may be mounted in any of the holes in the test plate. The x and z coordinates of this leak are unknowns in the signal processing routines.

Three leak rates were investigated: $10^{-2}$ cm$^3$/s (large enough to produce visible bubbles in a dunk tank), $1.22 \times 10^{-5}$ cm$^3$/s (approximately one cm$^3$ per day), and $6.38 \times 10^{-7}$ cm$^3$/s (approximately one cm$^3$ every two and a half weeks). The $10^{-2}$ cm$^3$/s leak was obtain ed using a needle valve from Leybold. The two smaller leaks are fixed-volume fixed-orifice calibrated leaks from Vacuum Instrument Corporation. The row of holes on the plate is interrogated using a Synrad grating-tuned 12 Watt $CO_2$ laser tuned to 10.6 microns which corresponds to a strong spectroscopic absorption band of $SF_6$ (Lymann et al. 1986). The nominal beam spot diameter of the $CO_2$ laser at the plate surface was 7 mm. Since the $CO_2$ laser is invisible it was combined with a 5 mW red He—Ne laser (not shown on FIG. 1) using a Zn—Se beam combiner to visualize the potentially-hazardous $CO_2$ beam. The laser beams are initially perpendicular to one another and each forms an incidence angle of 45 degrees with the beam combiner. The combined beams are then incident on a Lincoln Laser beam scanner consisting of a twenty-sided polygonal mirror mounted on the shaft of a high-speed motor that can rotate up to 37,500 rpm. The scanner motor is run at 18,750 rpm yielding a beam-scan rate of 6.25 kHz with a sweep angle of 30 degrees. The scanner sets up a line scan that is centered at normal incidence on the aluminum test plate located 0.84 m away. The scanned laser beams traverse the plate horizontally in the negative x-direction.

When the laser beam illuminates the tracer-gas cloud formed near the test leak, photoacoustic sound is generated at frequencies which are harmonics of the scan rate. This sound is then measured using two or four Brüel & Kjaer Model 4136 quarter-inch broadband microphones. The microphones have a nominal bandwidth from a fraction of a Hertz to about 80 kHz. The microphones form a linear array parallel to the x-axis and 0.41 meters away from the plate 14.6 cm above the optical table top. This vertical position allows the scanned laser beams to travel an unobstructed path beneath the microphones. The intended microphone spacing is 25.4 mm, slightly less than half of a wavelength at 6.25 kHz, with a nominal placement error of ±1 mm.

The measured sound from each microphone is high-pass filtered with a cutoff frequency of 3 kHz by a Krohn-Hite Model 3364 analog filter and acquired using a PC-based data acquisition system at a rate 104.667 kHz per channel for a 0.629 second data record duration. The acquired time domain signals are fast Fourier transformed, and the amplitude and phase of the signal at the harmonics of the scan rate are passed to the MFP routines to determine the location of the leak. MFP is carried out using the Bartlett processor, $B_B(r)$, the usual gage in MFP studies, and the MV processor $B_{MV}(r)$, a nonlinear processor that has the ability to reject correlated noise from locations other than the source location (Jensen et al. 1994). These processors were chosen because neither require a priori knowledge of background noise, and because they are representative of the two classes of matched-field processors: linear and nonlinear (or adaptive).

With m microphones located at positions $r_i=(x_i,y_i,z_i)$, the narrowband version of either the Bartlett processor or minimum variance distortionless (MV) processor at a frequency $\omega$ (rad/s) and location $r=(x,y,z)$, can be cast into the same form:

$$B(r;\omega) = \sum_{i=1}^{m}\sum_{j=1}^{m} w*(r,r_i;\omega)K_{ij}(\omega)w(r,r_j;\omega) \quad (1a)$$

where $B(r,\omega)$ is the processor output or ambiguity function, $w(r,r_i;\omega)$ is the weighting for each microphone, $K_{ij}$ is the measured cross spectral density matrix of the microphone measurements $M_i(\omega)$ at frequency $\omega$:

$$K_{ij}(\omega) = \frac{M_i*(\omega)M_j(\omega)}{\sum_{n=1}^{m}|M_n(\omega)|^2}, \quad (1b)$$

and the asterisk denotes complex conjugation. In some applications of MFP, $K_{ij}(\omega)$ is determined from an ensemble average of several independent sets of measurements (Baggeroer et al. 1993).

For the Bartlett processor, the microphone weights are determined from:

$$w_B(r,r_i)=G(r,r_i;\omega)/|G(r,r_i;\omega)| \quad (2)$$

where $G(r,r_i;\omega)$ is the appropriate Green's function for the Helmholtz equation at frequency $\omega$. The current experimental step-up approximates a quarter-space (y>0, z>0) with two hard walls at y=0 (the optical table top) and z=0 (the test plate), so the following Green's function based on the method of images was used:

$$G(r,r_i;\omega) = \frac{S_1 e^{ikr_1}}{4\pi r_1} + \frac{S_2 e^{ikr_2}}{4\pi r_2} + \frac{S_3 e^{ikr_3}}{4\pi r_3} + \frac{S_4 e^{ikr_4}}{4\pi r_4} \quad (3a)$$

where:

$$r_1 = \sqrt{(x-x_i)^2 + (y-y_i)^2 + (z+z_i)^2}, \quad (3bc)$$
$$r_2 = \sqrt{(x-x_i)^2 + (y+y_i)^2 + (z-z_i)^2},$$
$$r_3 = \sqrt{(x-x_i)^2 + (y-y_i)^2 + (z+z_i)^2}, \quad (3de)$$
$$r_4 = \sqrt{(x-x_i)^2 + (y+y_i)^2 + (z+z_i)^2},$$

k is the acoustic wave number, and $S_1$ through $S_4$ are the frequency- and direction-dependent microphone sensitivities. The environmental model of (3) treats the plate and table top as infinite in extent. Thus (3) remains valid as long as the leak is several fundamental-frequency wavelengths from the edge of the plate or the table. Simpler environmental models that neglect reflections from the plate and/or the optical table proved useless. More complicated models that account for reverberation within the laboratory were not found necessary. For the Bartlett processor, the weight vectors do not depend on $M_i$, so the processor is considered to be linear with respect to the received signals.

For the MV processor the received signals are used in the construction of the microphone weights to minimize the output of the processor for all locations except the location of the acoustic source. The MV weights explicitly depend on the measurements which renders this processor nonlinear;

$$w_{MV}(r,r_i;\omega) = \frac{\sum_{j=1}^{m}([K_{ij}(\omega)])^{-1}w_B(r,r_j;\omega)}{\sum_{i=1}^{m}\sum_{j=1}^{m}w_B(r,r_i;\omega)[K_{ij}(\omega)]^{-1}w_B(r,r_j;\omega)}. \quad (4)$$

Here, $[\ ]^{-1}$ implies a matrix inverse which becomes problematic when $K_{ij}$ does not have full rank. This problem occurs when m>1 but only one set of measurements $M_i(\omega)$ is used to construct $K_{ij}(\omega)$. In the current investigations, this matrix inversion problem was overcome by diagonal loading of $K_{ij}$ (Baggeroer et al. 1993) with 0.01 times the identity matrix ($\delta_{ij}$). The MV processor output is sensitive to the level of diagonal loading and alternate loading schemes are currently being considered.

For both processors, the extension from narrowband to multiple frequencies is accomplished by incoherently averaging the narrowband ambiguity functions:

$$B(r) = \frac{1}{N}\sum_{n=1}^{N} B(r,\omega_n) \quad (5)$$

where the number of signal frequencies is N.

As was mentioned previously, photoacoustics is the excitation of acoustic waves by unsteady heating from a light source. This unsteady heating shows up as a source term in the Helmholtz equation which has an integral solution of the following form:

$$\tilde{p}(r,w) = \frac{i\omega}{4\pi}\frac{\gamma-1}{c^2}\int_{all\,r'}\tilde{H}(r,\omega)G(r,r';\omega)d^3r' \quad (6)$$

Here $\tilde{p}$ is the complex pressure field, $\gamma$ is the field point, y is the ratio of specific heats of the ambient gas, c is the ambient speed of sound, and $\tilde{H}(r,\omega)$ is the temporal Fourier transform of the rate of heat produced per unit volume by the absorption of light. The integral is performed over the source coordinate r'. Increased absorption of light by the gas or increased light intensity leads to an increase in the source strength which in turn leads to an increase in the magnitude of the photoacoustic sound. In addition, higher frequencies are clearly favored in (6). Details of how the spectroscopic properties of a photoactive gas and its interaction with the light influence the heating term can be found in Kreuzer (1977) and Rosencwaig (1980).

Figure 2:
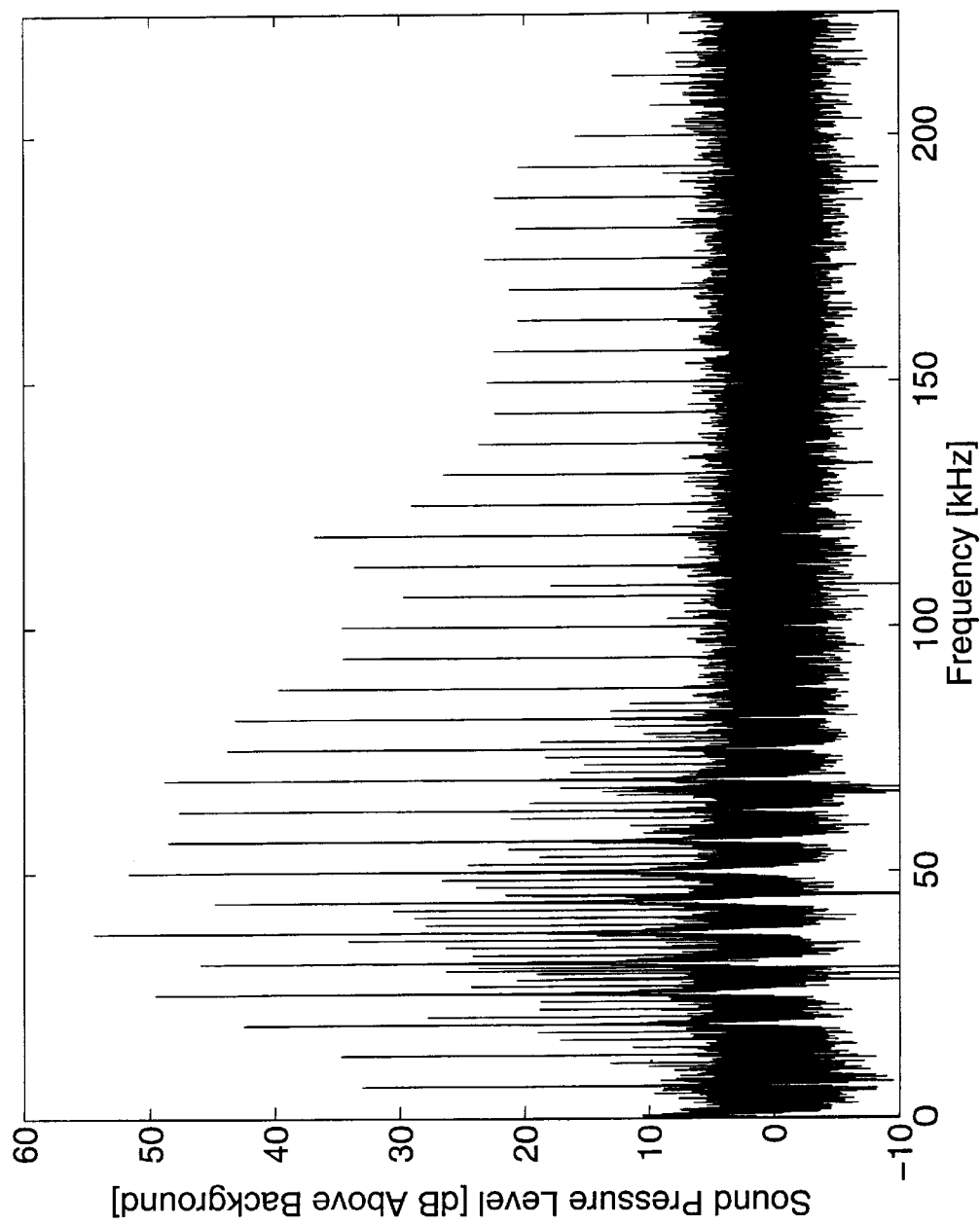
FIG. 2 illustrates a graphical representation of the FFT amplitude spectrum for the photoacoustic sound from a leak.

The photoacoustic sound is generated by rapidly scanning the $CO_2$-laser beam over the leaking gas. As the laser repeatedly passes over the gas cloud formed near the leak, the gas absorbs the laser light and repeatedly expands. This repeated unsteady expansion launches acoustic waves. A normalized FFT amplitude spectrum for the photoacoustic signal from the largest leak in this study, $10^{-2}$ cm$^3$/s, is displayed on FIG. 2. These measurements were made with a single microphone 0.41 m from the leak at a sampling rate of 500 kHz with the leak at x=z=0 (the middle of laser scan). The spectrum on FIG. 2 is normalized by an equivalent-length and bandwidth background noise spectrum measured with the whole experiment in operation but without a leak mounted on the plate. Hence, spectral values near 0 dB correspond to the noise level. The fluctuations of ±5 dB near 0 dB result from non-repeatability in the noise and are not statistically significant. The fundamental frequency of the photoacoustic sound is 6.25 kHz (the laser beam scan rate). FIG. 2 shows that the dominant tones of the photoacoustic signal are this fundamental frequency and its first 35 harmonics up to approximately 225 kHz. The bias toward the higher frequency harmonics predicted by (6) can be deduced from FIG. 2 where tonal signal components are clearly evident well beyond the nominal microphone bandwidth of 80 kHz. These high frequency signal tones must be loud enough to overcome the loss of microphone sensitivity. The secondary signal tones that occur between the main signal harmonics from approximately 10 kHz to 80 kHz are believed to be caused by modulation of the spinning speed of the rotating-polygonal-mirror laser scanner which is driven by a four-pole motor. These secondary tones are spaced at intervals that are one fourth of the fundamental frequency which is consistent with scan-rate modulation produced by the rotational-speed fluctuation characteristics of a four pole motor.

It was found that the photoacoustic signal frequencies are stable within the limits set by the motor controller for the rotating polygonal mirror. However, the signal amplitudes and the phase relationship between signal harmonics varied from trial-to-trial making it impossible to exploit any form of coherent broadband processing. These signal fluctuations are believed to be caused by motion and deformation of the tracer gas cloud formed near the leak, and are the subject of on going investigation.

Figure 3:
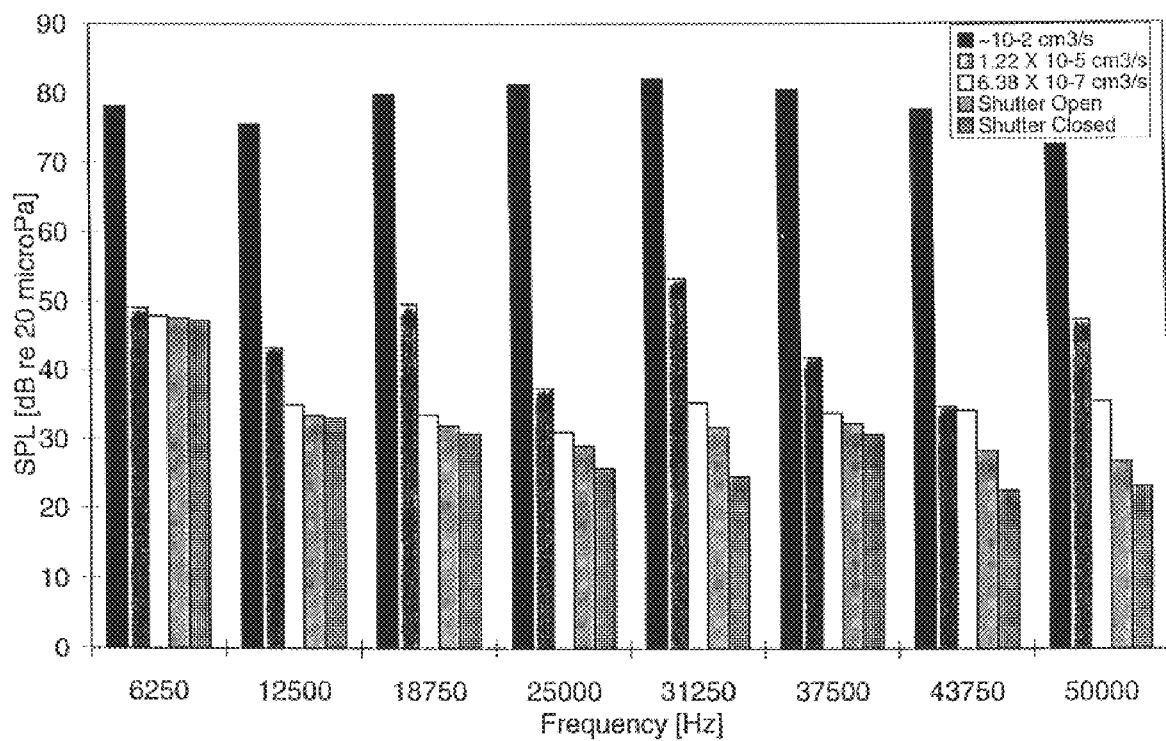
FIG. 3 illustrates average photoacoustic signal amplitudes for the first eight signal harmonics of an experimental set-up for the invention.

The leak-rate dependence of the average amplitude received by the four-microphone array at the first eight signal frequencies is shown on FIG. 3 along with two measurements of the background noise. In all five cases shown on FIG. 3, the FFT amplitudes from the four microphones are converted to sound-pressure amplitude using the manufacturer's calibration of microphone sensitivity, averaged, and converted to sound pressure level (dB re 20 $\mu$Pa). Both of the background sound measurements were made without a leak mounted on the plate but with all of the other experimental components switched on. In one case the $CO_2$-laser shutter is open, and in the other it is closed. The second noise check is made to quantify the photoacoustically-generated background noise from the laser beam scanning over the plate alone. The shutter-open noise level is the more important from a leak-detection performance standpoint. FIG. 3 clearly shows the $10^{-2}$ cm$^3$/s leak to be the loudest, and this leak is easily audible in the laboratory. The two smaller leaks produce average signal amplitudes still exceeding, but much closer to, the background noise level.

Based on these results, it should be possible to use the amplitude of the recorded sounds at several of the dominant signal frequencies to determine whether or not a leak is present by simple thresholding. The $10^{-2}$ cm$^3$/s leak is 30 dB or more above the shutter-open noise level at every signal frequency. The $1.22 \times 10^{-5}$ cm$^3$/s leak is more than 10 dB above the shutter-open noise level at five of the eight signal frequencies. The $6.38 \times 10^{-7}$ cm$^3$/s leak is only a few dB above the shutter-open noise level at the eight signal frequencies. Hence, a detection threshold of several dB above background at selected signal frequencies should provide satisfactory detection performance for leaks larger than $10^{-5}$ cm$^3$/s. For the present experiments, a 9 dB threshold applied at signal frequencies of 18.75 kHz, 31.25 kHz, 37.5 kHz, and 50.0 kHz detected the two larger leaks without the fail or false detection for more than 50 trials. However, with this simple threshold scheme the smallest leak could not be detected about half the time and the false detection probability also approached 50%. Improved detection capability at the lowest leak rate may be possible with more microphones, shorter path lengths, or use of a more sophisticated signal detection scheme, such as that described for the leak localization in the next section.

It should be noted that there is significant background photoacoustic sound generated by the interaction of the laser and aluminum plate alone. For example, by comparing the two background sound levels on FIG. 3, the photoacoustic sound (noise) at 31.25 kHz generated by scanning the $CO_2$ laser across plate alone is 7.1 dB above the noise level when the $CO_2$-laser shutter is closed. Ultimately, any leak detection limit will be set by correlated noise generated by the target device on which the leak resides.

Once the presence of a leak is determined, the next step is to find its location. As discussed above, this was approached using the measured photoacoustic signals and the Bartlett and MV matched field processors. The computation of the necessary replica fields was done using (3) for the eight lowest signal frequencies. The higher signal harmonics reside beyond the capability of the current data acquisition system when four input channels are used. The eight single-frequency ambiguity surfaces were averaged according to (5). The rest of this section describes how microphone number, processor type, leak rate, and leak/microphone geometry influence photoacoustic leak localization.

Figure 4:
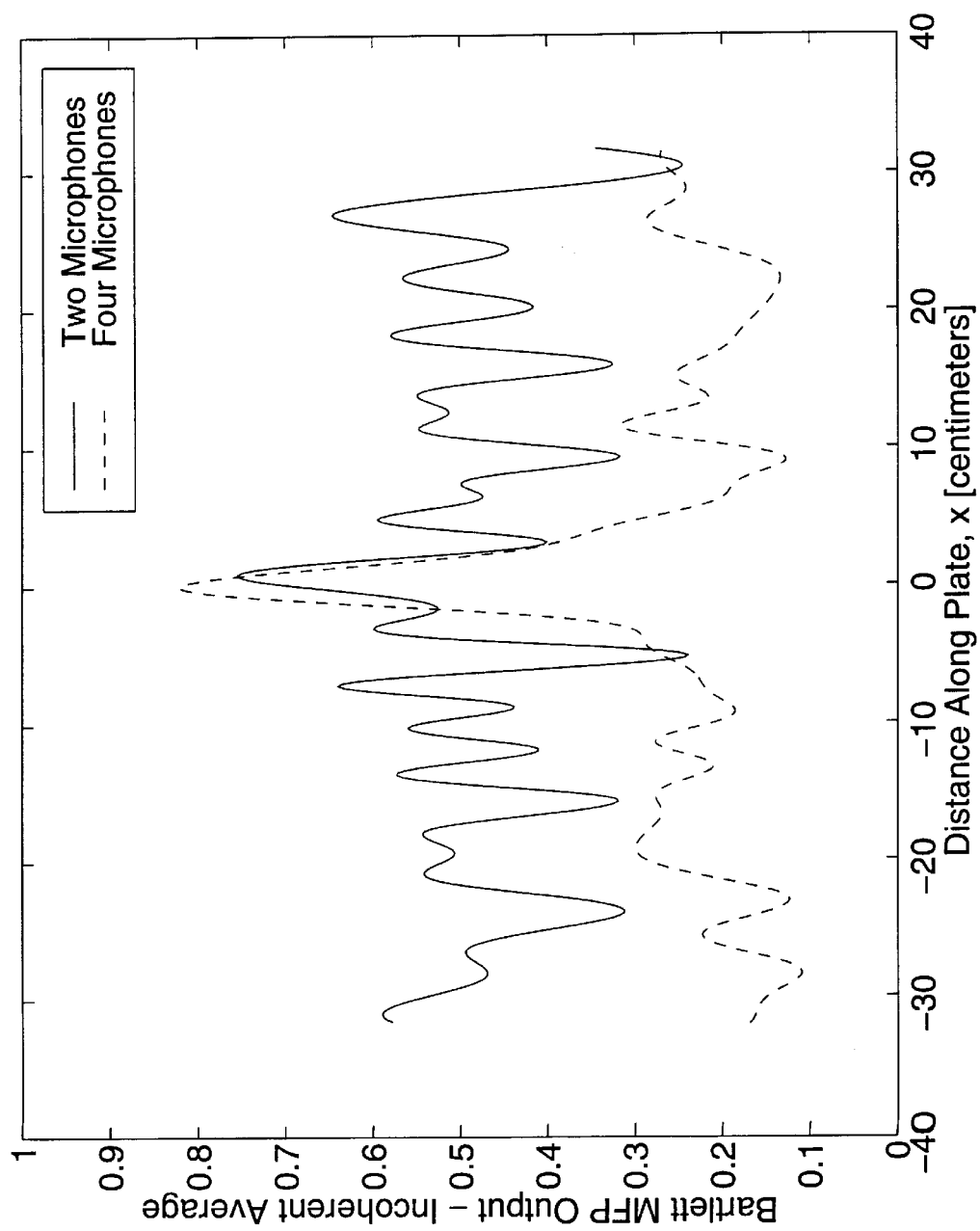
FIG. 4 illustrates the multiple-frequency Bartlett MFP results.

The first comparison is drawn between the use of two and four microphones for the Bartlett processor with the $1.22 \times 10^{-5}$ cm$^3$/s leak located at the center of the plate. The intersection of the multiple-frequency ambiguity surface with the plane of the plate (z=0) is displayed on FIG. 4. The horizontal axis is the distance along the plate with x=0 denoting the plate center. Here, the leak is known to lie on the surface of the plate so only results from z=0 need to be examined. The peak value of these MFP results gives the processor-determined location of the leak along the line of the laser scan (the x-direction). Although, FIG. 4 shows that x-direction localization is possible with two microphones, the four microphone results are clearly superior. The two-microphone side lobes are 13% below the peak while the four microphone side lobes are 62% below the peak. Moreover, the two microphone results indicate a leak location that is 6 mm to the right of center, while the four microphone localization agrees with actual leak location to within less than 1 mm.

Figure 5A:
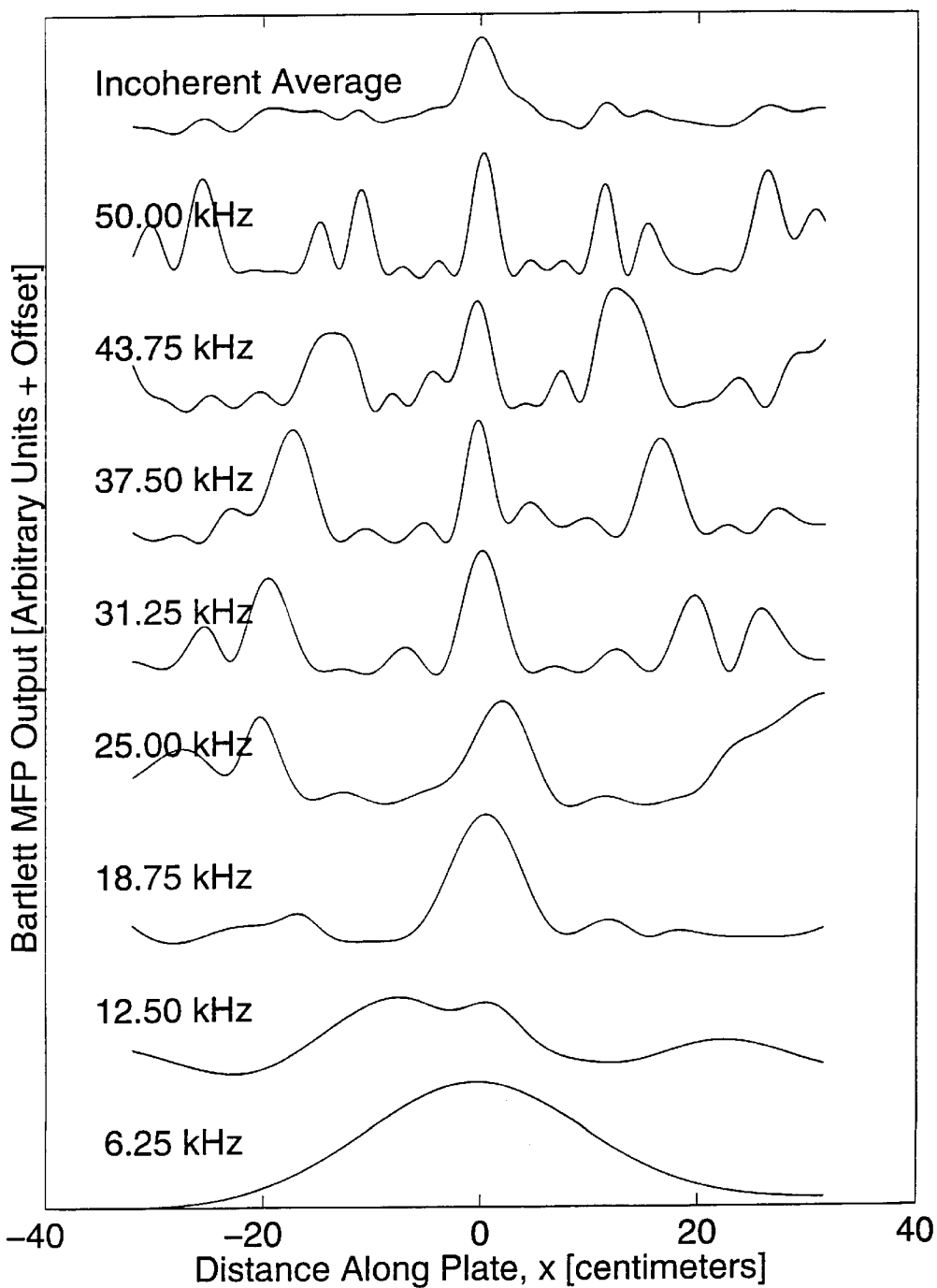
FIG. 5A illustrates frequency by frequency and incoherent-average MFP results for the Bartlett processor.
Figure 5B:
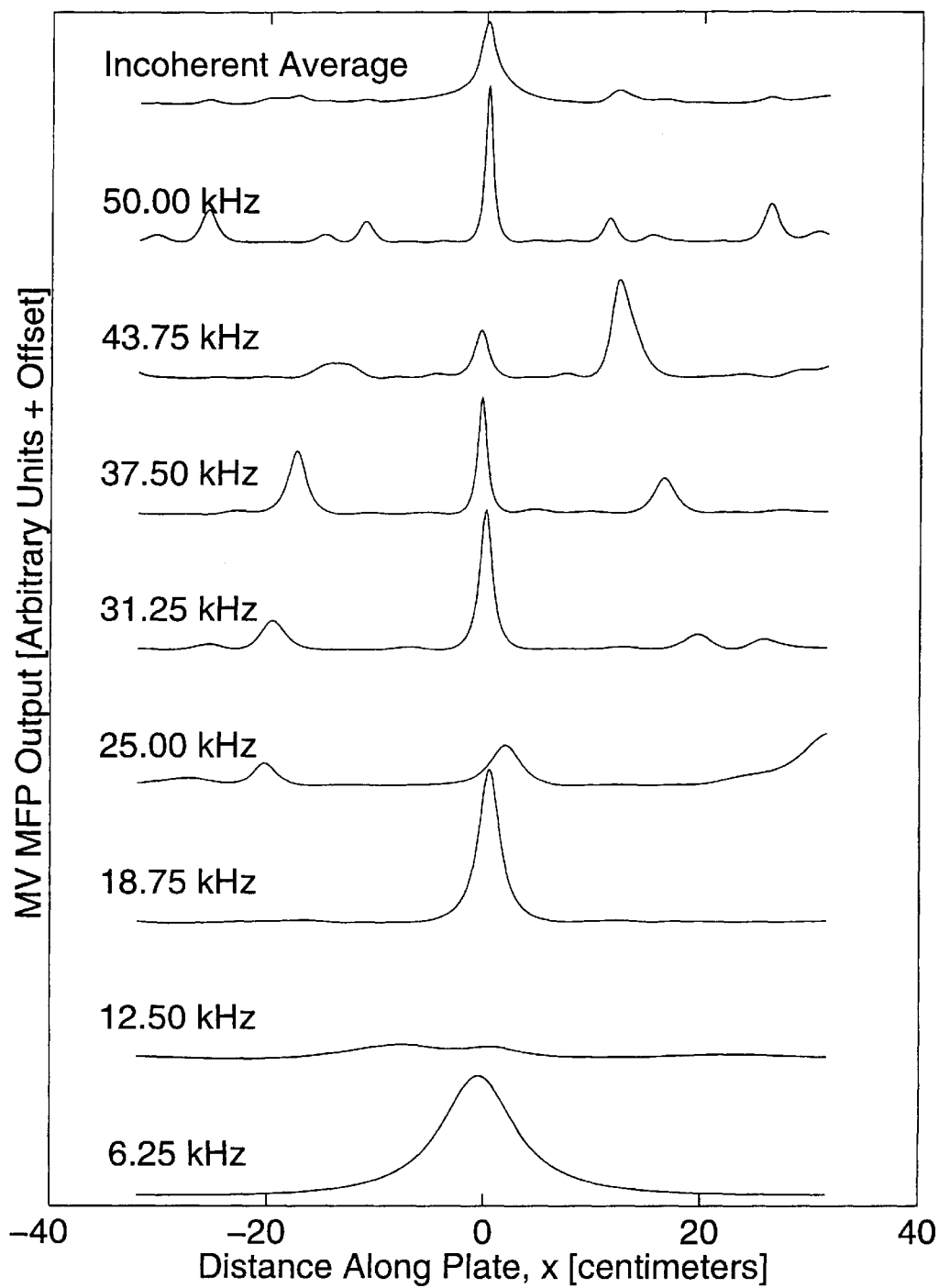
FIG. 5B illustrates frequency by frequency and incoherent-average MFP results for the minimum variance distortionless (MV) processor.

A comparison of the differences between single- and multiple-frequency MFP is shown by FIGS. 5A and 5B which display the various single-frequency and the incoherent-average ambiguity surfaces for variable x at z=0 for the $1.22\times10^{-5}$ cm$^3$/s leak located at x=0 when four microphones are used. For the Bartlett processor (FIG. 5*a*), the leak is unambiguously localized at the center of the plate at 6.25 and 18.75 kHz, but the spatial resolution at these frequencies is relatively low yielding broad ambiguity peaks. At frequencies 25 kHz and higher, the ambiguity peaks are narrower but now there are significant spatial side lobes. In fact, at 43.75 kHz the side lobe magnitude is greater than that of the main lobe. The incoherent average (the top trace on FIG. 5*a*) reduces spatial side lobes yet partially retains the spatial resolution associated with the higher frequencies. For the MV processor in (FIG. 5*b*) the peaks are narrower and the side lobe suppression is usually better. However, the main peak is sometimes suppressed in favor of a side lobe.

Figure 6A:
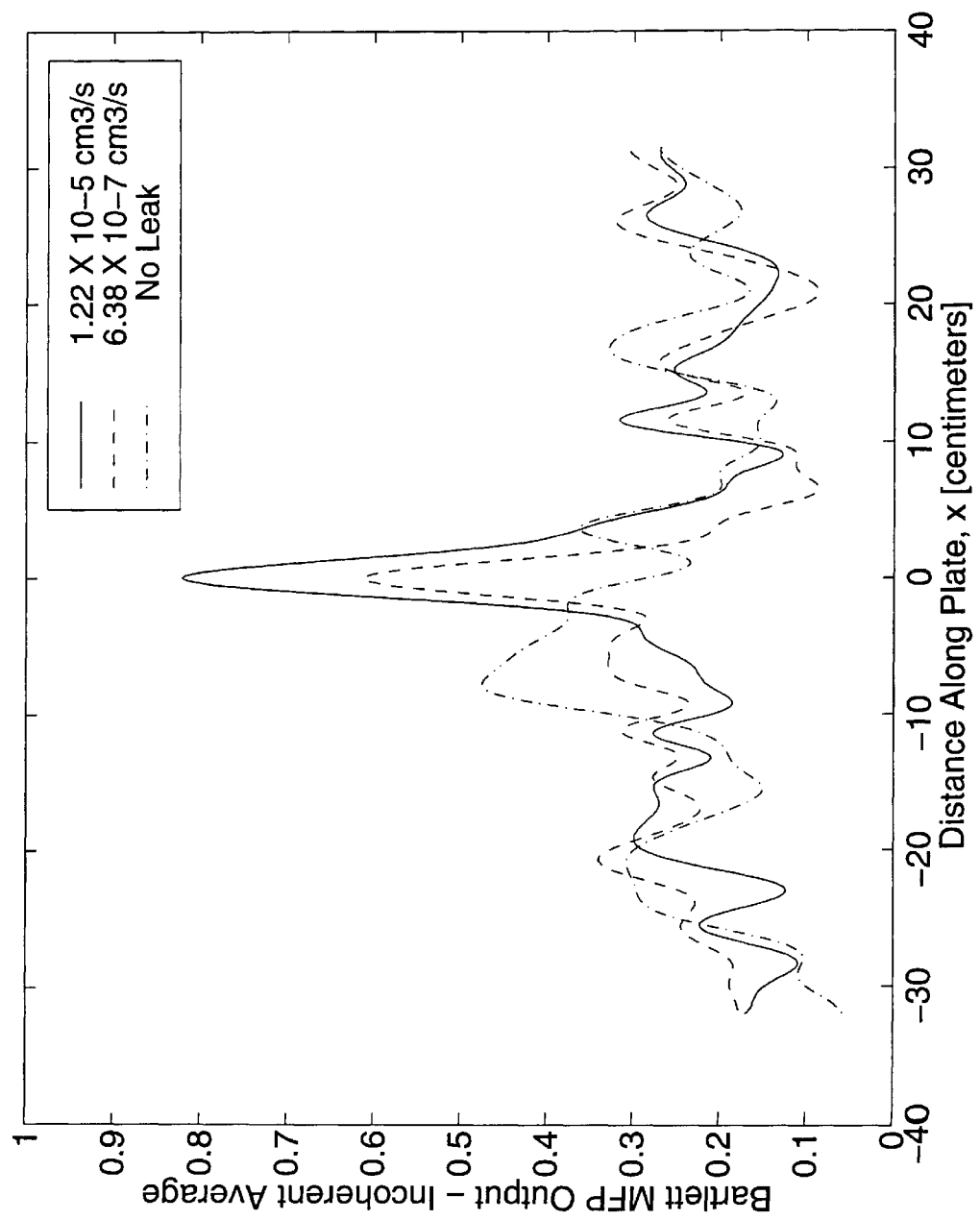
FIG. 6A illustrates a comparison of incoherently averaged MFP results for the Bartlett processor.
Figure 6B:
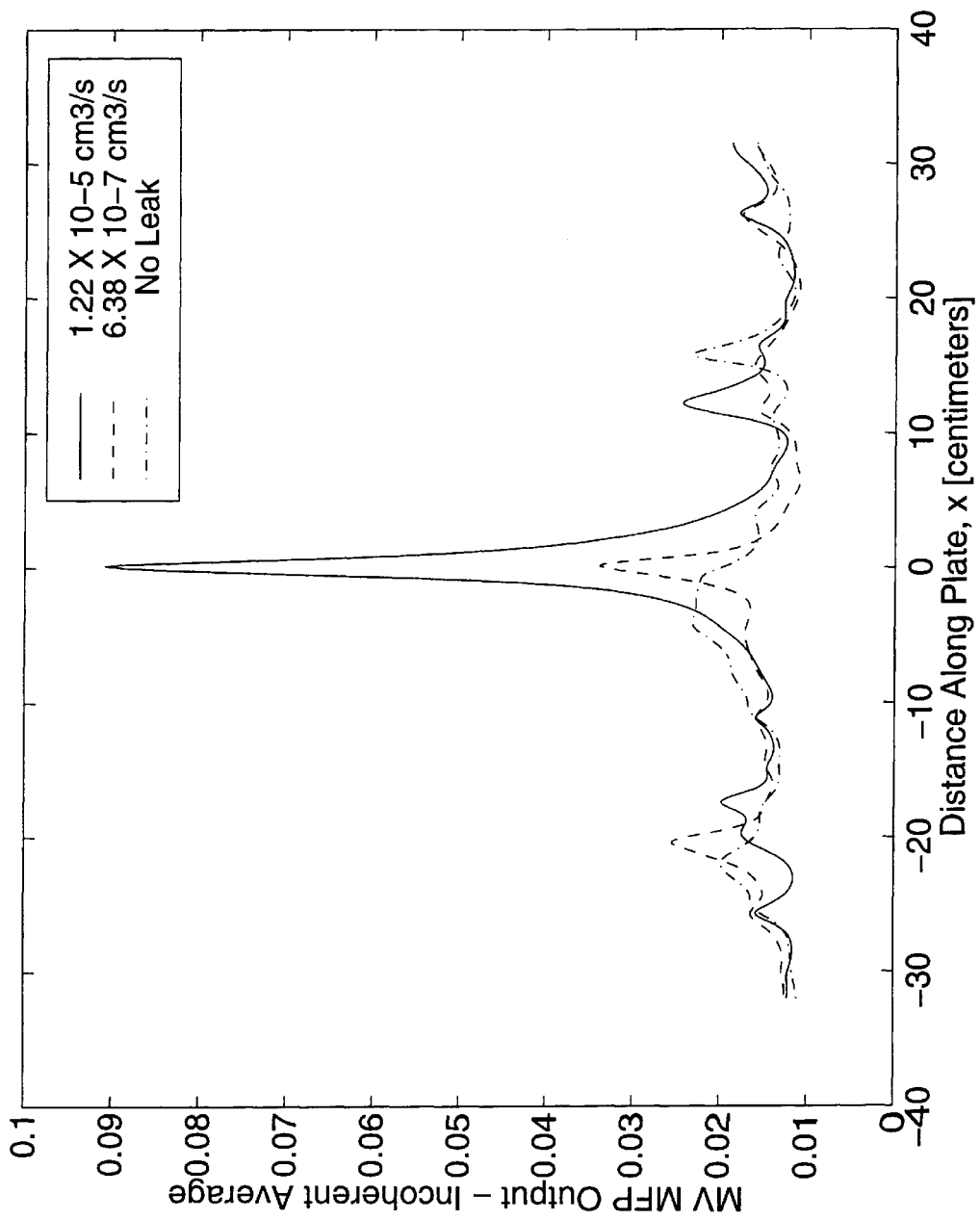
FIG. 6B illustrates a comparison of incoherently averaged MFP results for the minimum variance distortionless (MV) processor.

The effect of leak size is provided by a comparison of the Bartlett (FIG. 6A) and MV (FIG. 6B) processors for variable x at z=0. In both FIGS. 6A and 6B, MFP output for the $1.22\times10^{-5}$ cm$^3$/s and the $6.38\times10^{-7}$ cm$^3$/s leaks placed at x=0 are each compared to a representative case when no leak is present. The no-leak results vary from trial-to-trial because of noise fluctuations. Note that the vertical scale of FIG. 6*b* is expanded relative to that of FIG. 6*a*. The $1.22\times10^{-5}$ cm$^3$/s leak is easily localized by both processors with the main ambiguity peak at least twice as high as any false-localization peak of the no-leak case. The MV results for this leak exhibit a narrower main lobe implying a finer localization resolution. The smaller $6.38\times10^{-7}$ cm$^3$/s leak is also found by both processors. However, the main lobe magnitude for both processors is reduced: by 25% for the Bartlett processor, and by almost 70% for the MV processor. All the results on FIGS. 2 through 6 have been for leaks located at x=0.

Figure 7A:
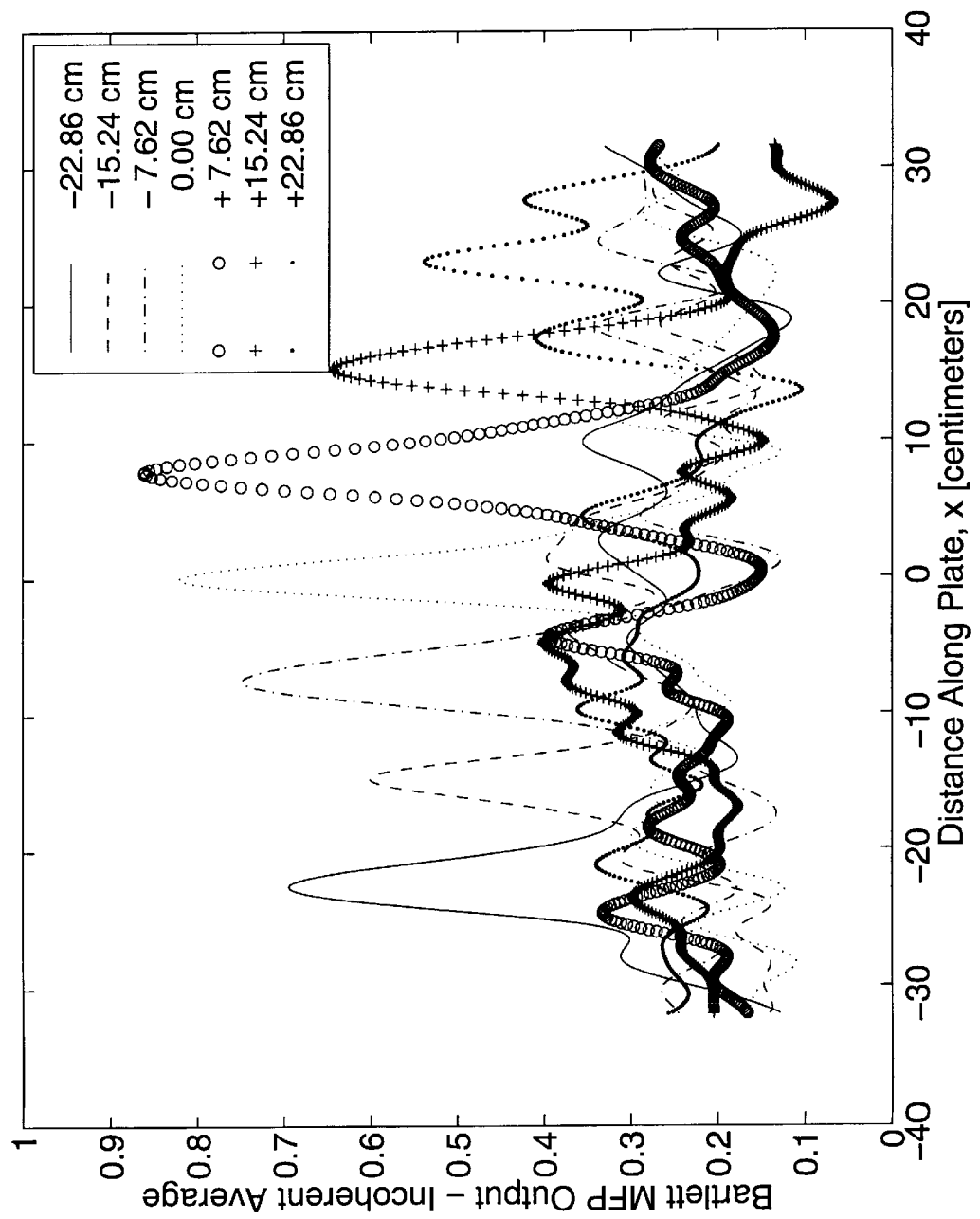
FIG. 7A illustrates incoherently averaged MFP results for the Bartlett processor.
Figure 7B:
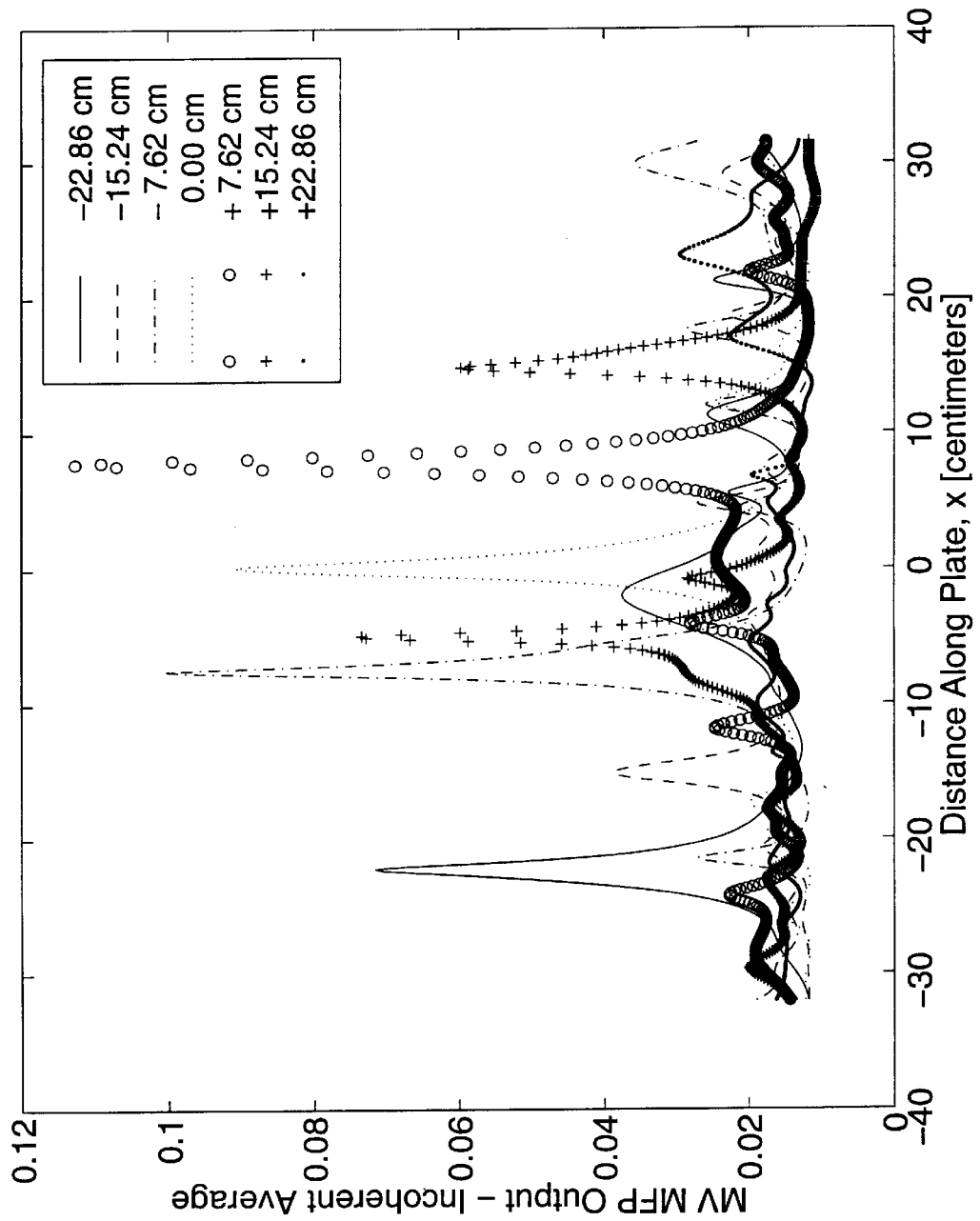
FIG. 7B illustrates incoherently averaged MFP results for the minimum variance distortionless (MV) processor.
Figure 8:
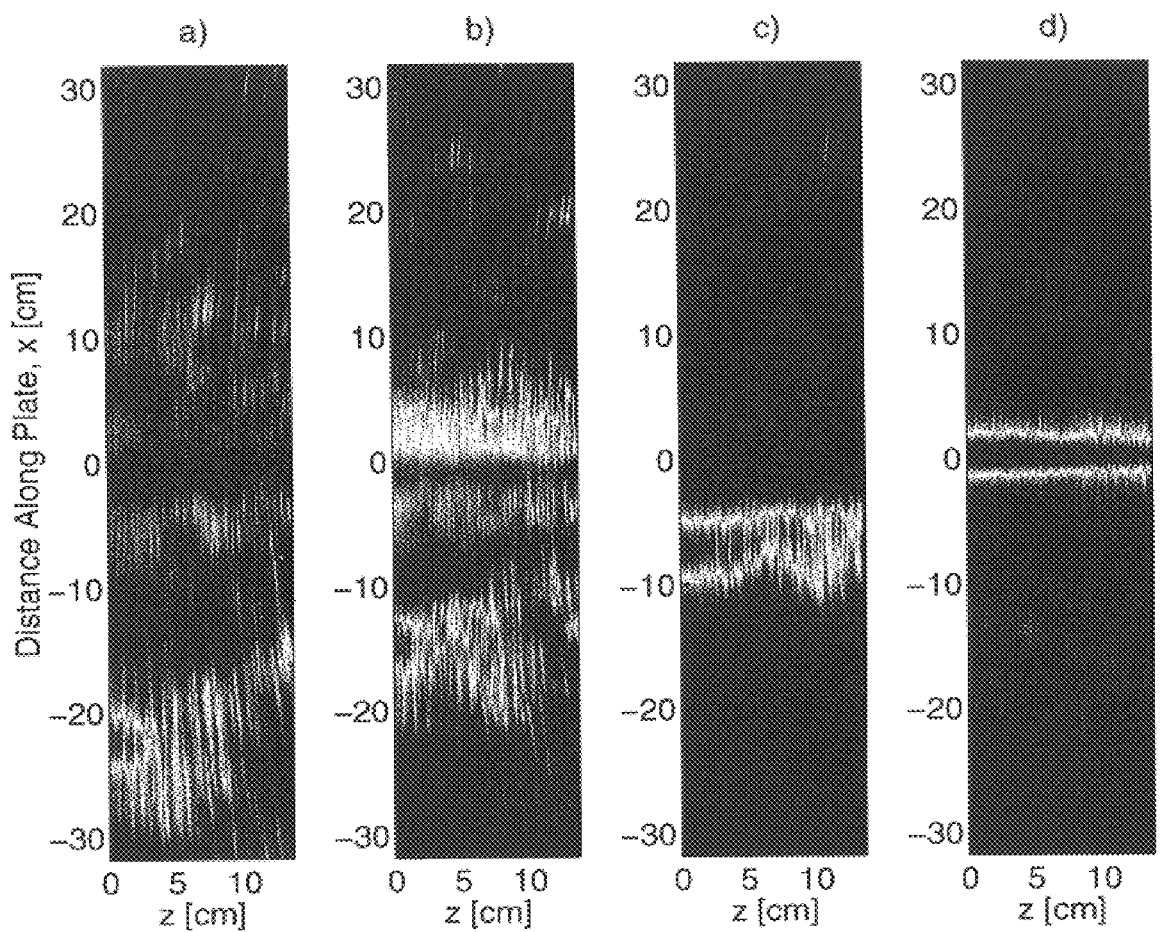
FIG. 8 illustrates Bartlett MFP ambiguity surfaces computed in the x-z plane.
Figure 9:
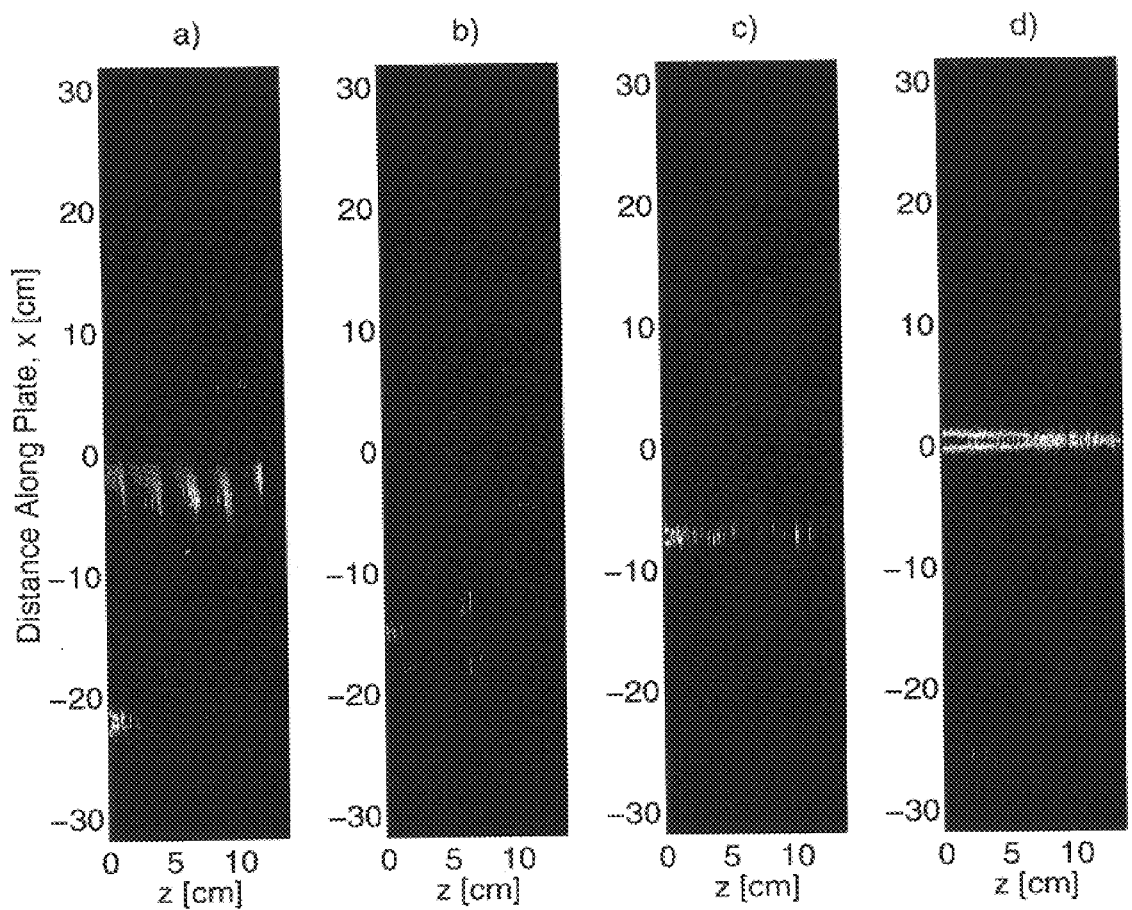
FIG. 9 illustrates MFP ambiguity surfaces computed in the x-z plane for the minimum variance distortionless processor.

Intersection of the incoherent-average ambiguity surfaces with the plate surface (z=0) are shown for the Bartlett (FIG. 7A) and MV (FIG. 7B) processors when all four microphones are used and the $1.22\times10^{-5}$ cm$^3$/s leak is located at seven different locations: x=−22.86, −15.24, −7.62, 0, +7.62, +15.24, +22.86 cm. The Bartlett processor locates this leak at all seven positions to within ±3 mm. The MV processor locates the leak successfully in six of the seven locations. It fails when the leak is placed at x=+15.24 cm because of a side peak near x =−6 cm. In addition, the main lobe peaks when the leak is a x=−22.86, −15.24 cm and +22.86 cm are all lower than the side lobe peak when the leak is at x=+15.24 cm. Peak/side-lobe amplitude overlap of this kind have thus far prevented the development of a leak-detection criterion based on MFP, although investigations are continuing and improvements may be possible with other processors.

As a further illustration of the results given in FIGS. 7A and 7B, FIGS. 8 and 9 show x-z ambiguity surface plots for the Bartlett and MV processors, respectively, for four cases when the $1.22\times10^{-5}$ cm$^3$/s leak is located at x=−22.86, −15.24, −7.62, and 0 cm. For both processors, the results are somewhat symmetric about x=0. The views shown are those obtained by looking down upon the processing grid shown in FIG. 1. A comparison of FIGS. 8 and 9 reveals that the MV processor generally provides better spatial resolution than the Bartlett processor, which is consistent with its performance in underwater applications (Jensen et al. 1994). For both processors, as the leak is moved to away from the center of the plate, the z-coordinate of the leak is determined in addition to its x-coordinate. This shows that asymmetry and complexity in the acoustic environment actually aids leak localization, a phenomena previously described in underwater acoustics as environmental signal processing (Perkins and Kuperman, 1990).

The comparison between the Bartlett and MV processors presented on FIGS. 5 through 9 can be summarized as follows. The MV processor has greater side lobe suppression capability and a narrower main lobe than the Bartlett processor at a single frequencies when the photoacoustic signal is strong enough. However, when the results are incoherently averaged the side lobe suppression capability of both processors is essentially equal but the MV processor continues to have a narrower main lobe than the Bartlett processor. The multiple-frequency Bartlett processor appears to have an advantage at low signal-to-noise ratios because its side lobe structure remains benign.

To determine the sensitivity of leak location error to random error in microphone placement and speed of sound mismatch, Monte Carlo simulations of the experiment with the Bartlett processor were performed. The results of the simulation show that a root-mean-square (rms) error in microphone placement of 1 mm in each coordinate direction leads to approximately 6 mm rms error in leak location. The sensitivity to mismatch between the actual sound speed in the lab during an experiment, and the computed sound speed based on the measured temperature is predicted to be less important. A mismatch of 0.6 m/s (corresponding to a temperature error 1.0° C. in air at ordinary room conditions), should lead to and rms error of 1 mm in leak location. Hence, the observed leak location accuracy of ±3 mm for the $1.22\times10^{-5}$ cm$^3$/s leak easily falls within the bounds of the microphone placement error, but is larger than that likely to be caused by mismatch in the speed of sound.

Having described the invention, many modifications thereto will become apparent to those skilled in the art to which it pertains without deviation from the spirit of the invention as defined in the appended claims.

What is claimed is:

1. A system for the detection and localization of gas emitted from a container, the system comprising:

a light source for producing non-pulsing light;

means for scanning said non-pulsing light across a surface of the container;

a light source for producing visible light colinear with the non-pulsing light for visualizing the non-pulsing light;

a photoactive tracer gas pressurized within said container;

means for detecting photoacoustic sound; and means for processing said photoacoustic sound, said means for processing said photoacoustic sound being non-synchronous with said means for scanning said non-pulsing light, wherein said non-pulsing light excites said gas leaking from said container creating a photoacoustic sound with said means for detecting the photoacoustic sound, and said means for processing said photoacoustic sound non-synchronously with said means for scanning said non-pulsing light.

2. The system according to claim 1 wherein non-pulsing said light source comprises a carbon dioxide laser operating at a wavelength of 10.6 microns.

3. The system according to claim 1 wherein the light source for producing visible light colinear with the non-pulsing light for visualizing the non-pulsing light comprises a helium-neon laser.

4. The system according to claim 1 wherein said photo-active tracer gas comprises sulfur hexafluoride.

5. The system according to claim 1 wherein said means for detecting photoacoustic sound comprises a multiplicity of microphones.

6. The system according to claim 1 wherein said means for detecting photoacoustic sound comprises detecting said sound across a broad bandwidth.

7. The system according to claim 6 wherein said broad bandwidth comprises 3 to 52 kHz.

8. The system according to claim 1 wherein said means for detecting photoacoustic sound comprises detecting said sound across all signal frequencies.

9. The system according to claim 1 further comprising means for recognizing an acoustic wave generated by the excitation of the gas by the light source.

10. The system according to claim 1 wherein said means for processing said photoacoustic sound comprises comparison of the acoustic environment and matched field processing.

11. The system according to claim 10 wherein said matched field processing comprises Bartlett processing.

12. The system according to claim 10 wherein said matched field processing comprises minimum variance processing.

13. The system according to claim 1 wherein the non-synchronous means for processing comprises signal processing means for discriminating the acoustic wave signal of the excited gas from the background noise.

14. The system for the detection and localization of gas emitted from a container according to claim 1 wherein the means for detecting photoacoustic sound comprises fewer than five microphones.

15. The system for the detection and localization of gas emitted from a container according to claim 14 wherein the fewer than five microphones are located in stationary positions.

16. A system for the detection and localization of gas emitted from a container, the system comprising:
    a light source for producing non-pulsing light;
    means for scanning said non-pulsing light across a surface of the container; a photoactive tracer gas pressurized within said container,
    means for detecting photoacoustic sound; and
    means for processing said photoacoustic sound, said means for processing said photoacoustic sound being non-synchronous with said means for scanning said non-pulsing light, wherein said non-pulsing light excites said gas leaking from said container creating a photoacoustic sound with said means for detecting the photoacoustic sound, and said photoacoustic sound being the fundamental frequency and harmonics of the fundamental frequency, said harmonics being multiple frequencies across all the frequency ranges, said means for processing said photoacoustic sound non-synchronously with said means for scanning said non-pulsing light.

17. The system for the detection and localization of gas emitted from a container according to claim 16 wherein the photoacoustic sound being the fundamental frequency and harmonics of the fundamental frequency, said harmonics being multiple frequencies across all the frequency ranges up to approximately 225 kHz.).

18. A method for detecting and then locating a leak from a container being tested according to the system of claim 16, the method comprising the following steps:
    pressurizing a container with a tracer gas;
    scanning a surface of the container with a collimated light source;
    detecting acoustic emissions across a broad bandwidth generated by the tracer gas upon excitation by the collimated light source; and
    processing a signal generated by the acoutic emissions by matched field processing non-synchronously with the scanning of the surface.

19. A system for detecting and localizing a gas leak emerging from a gas-tight or liquid-tight component under test comprising:
    a light source for providing a collimated light beam at a wavelength strongly absorbed by the leaking gas;
    beam scanning means optically aligned with said light source for scanning said light beam across said component under test in a predetermined pattern;
    acoustic detection means for detecting broadband acoustic waves generated by said leak upon absorption of said light beam and for producing an electrical signal proportional to the acoustic emission; and
    signal processing means non-synchronous with the beam scanning means, the signal processing means receiving a signal from said acoustic detection means for extracting gas leak acoustic emissions from background acoustic emissions and generating a leak indication signal, said signal processing means being matched field processing.

20. An improvement to a system for detecting and localizing a gas leak emerging from a gas-tight or liquid-tight component under test, the system comprising:
    a light source for providing a collimated light beam at a wavelength strongly absorbed by the leaking gas;
    beam scanning means optically aligned with said light source for scanning said light beam across said component under test in a predetermined pattern;
    acoustic detection means for detecting acoustic waves generated by said leak upon absorption of said light beam and for producing an electrical signal proportional to the acoustic emission; and
    signal processing means receiving a signal from said acoustic detection means for extracting gas leak acoustic emissions from background acoustic emissions and generating a leak indication signal,
    the improvement comprising:
        acoustic detection means for detecting broadband acoustic waves;
        signal processing means being non-synchronous with said beam scanning means; and
        said signal processing means being matched field processing.

* * * * *

UNITED STATES PATENT AND TRADEMARK OFFICE
CERTIFICATE OF CORRECTION

PATENT NO.   : 6,227,036 B1
DATED        : May 8, 2001
INVENTOR(S)  : Serdar H. Yonak and David R. Dowling It is certified that error appears in the above-identified patent and that said Letters Patent is hereby corrected as shown below:

Title page,
OTHER PUBLICATIONS, line 18, please replace "MAtched" with -- Matched --; and line 19, please replace "MEthods" with -- Methods --.

Column 1,
Line 28, after "processing.", please start a new paragraph with "Photoacoustics";
Line 56, before "Matched Field", please insert -- broadband --;

Column 2,
Line 14, please make the 2 in "CO2" a subscript;
Line 15, please delete "calibrated";

Column 3,
Line 18, please delete "a flat plate" and insert -- the part being tested --;
Lines 18 and 19, please delete "of known rate";

Column 4,
Line 8, please replace "noise" with -- sound --;
Line 9, please replace "noise" with -- sound --;
Line 26, please replace "a re" with -- are --;
Line 32, please delete "known rate";
Line 36, for the numeral 10, please replace the superscript with the superscript -- -2 --;
Line 38, for the numeral 10, please replace the superscript with the superscript -- -5 --;
Line 40, for the numeral 10, please replace the superscript 2 with the superscript -- -2 --; and please delete "obtain ed" and replace with -- obtained --;

UNITED STATES PATENT AND TRADEMARK OFFICE
CERTIFICATE OF CORRECTION

PATENT NO. : 6,227,036 B1
DATED : May 8, 2001
INVENTOR(S) : Serdar H. Yonak and David R. Dowling It is certified that error appears in the above-identified patent and that said Letters Patent is hereby corrected as shown below:

Column 5,
Line 55, please replace equation (2) with $$w_B(\mathbf{r},\mathbf{r_i}) = G(\mathbf{r},\mathbf{r_i};\omega)/\left[\sum_{i=1}^{N} |G(\mathbf{r},\mathbf{r_i};\omega)|^2\right]^{1/2} \quad ;$$

Column 6,
Line 61, please delete "γ" and replace with bold lower case -- r --; and
Line 62, please delete "y" and replace with -- γ --.

Signed and Sealed this

Twenty-third Day of April, 2002

*Attest:*

*Attesting Officer*

JAMES E. ROGAN
*Director of the United States Patent and Trademark Office*